(12) United States Patent
Massengale et al.

(10) Patent No.: US 7,100,771 B2
(45) Date of Patent: Sep. 5, 2006

(54) PAIN MANAGEMENT KIT FOR ADMINISTRATION OF MEDICATION

(75) Inventors: Roger Dillard Massengale, Mission Viejo, CA (US); Robert B. Keahey, San Antonio, TX (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 11/178,648

(22) Filed: Jul. 11, 2005

(65) Prior Publication Data

US 2005/0241986 A1 Nov. 3, 2005

Related U.S. Application Data

(63) Continuation of application No. 10/796,630, filed on Mar. 9, 2004, now abandoned, which is a continuation of application No. 10/123,436, filed on Apr. 15, 2002, now abandoned.

(60) Provisional application No. 60/283,800, filed on Apr. 13, 2001.

(51) Int. Cl.
*B65D 71/00* (2006.01)
*A61B 19/02* (2006.01)

(52) U.S. Cl. .................. 206/570; 206/363; 206/370; 206/438

(58) Field of Classification Search ............. 206/363, 206/364, 365, 366, 370, 570, 571, 438
See application file for complete search history.

(56) References Cited

U.S. PATENT DOCUMENTS

| | | | |
|---|---|---|---|
| 3,329,261 A | 7/1967 | Serany, Jr. et al. | |
| 3,650,393 A | 3/1972 | Reiss et al. | |
| 3,770,119 A | 11/1973 | Hultberg et al. | |
| 4,170,300 A | 10/1979 | Pick | |
| 4,266,669 A | 5/1981 | Watson | |
| 4,501,363 A | 2/1985 | Isbey, Jr. | |
| 4,522,302 A | 6/1985 | Paikoff | |
| 4,595,102 A | 6/1986 | Cianci et al. | |
| 4,736,850 A | 4/1988 | Bowman et al. | |
| 5,174,306 A | 12/1992 | Marshall | |
| D343,687 S | 1/1994 | Houghton et al. | |
| 5,392,917 A | 2/1995 | Alpern et al. | |
| 5,779,053 A | 7/1998 | Partika et al. | |
| 6,840,379 B1 * | 1/2005 | Franks-Farah et al. | 206/571 |
| 6,926,708 B1 * | 8/2005 | Franks-Farah et al. | 604/544 |

OTHER PUBLICATIONS

Veins News, "Changing the Field of Pain Management" by Sheila Dwyer, Dec. 20, 2000.
Orsoftware Newsletter, "FDA Approves HDC's Nerve Block Infusion Kit", Nov. 4, 2000.
HomeCare, "Briefly Noted" by HomeCare Magazine Staff, Oct. 1, 1999.

* cited by examiner

*Primary Examiner*—David T. Fidei
(74) *Attorney, Agent, or Firm*—Knobbe, Martens, Olson & Bear LLP

(57) ABSTRACT

A pain management kit for the administration of medication and a related method of use is disclosed. The pain management kit includes the primary medical supplies for performing a continuous nerve block procedure, preferably in a single, sterile container. Specifically, the kit may contain medical supplies to create a sterile field, perform a local anesthetic procedure and to perform a continuous nerve block procedure. Preferably, the contents of the kit are arranged in the general order of their use.

8 Claims, 8 Drawing Sheets

PAIN MANAGEMENT KIT FOR ADMINISTRATION OF MEDICATION

RELATED APPLICATIONS

This application is a continuation of U.S. application Ser. No. 10/796,630, filed Mar. 9, 2004, abandoned, which is a continuation of U.S. application Ser. No. 10/123,436, filed Apr. 15, 2002, abandoned, which claims priority from, U.S. Provisional Patent Application No. 60/283,800, filed Apr. 13, 2001, the entireties of which are hereby incorporated by reference.

BACKGROUND OF THE INVENTION

1. Field of the Invention

This invention relates to pain management systems, and more specifically to a catheter-based infusion system for the administration of fluids. Most specifically, this invention relates to a pain management kit for performing a nerve block procedure.

2. Description of the Related Art

Prior to performing a surgical operation on a part of the body, such as for example the arms or legs, it may be desirable to perform a nerve block in order to anesthetize a nerve bundle in a part of the body proximate to where surgery will occur. Often, a catheter-based infusion system is utilized to both block the nerve bundle for surgery and to provide a continuous, low flow rate of the anesthetic over a period of time (e.g., 2–3 days following surgery) for post-operative pain management.

One approach is to use an epidural needle having an integral conductive wire such that a small amount of current may be pulsed through the needle by a nerve stimulator (i.e., a current generator). When the epidural needle is probed into the general area of the desired nerve bundle, the pulsing current stimulates the nerve and causes a motor response to assist in properly locating the needle. Once proper location of the needle is achieved, a test dose of the anesthetic may be provided through the epidural needle. Proper positioning of the needle is verified by a failure to obtain a motor response to the current stimulation. At this point, a catheter may be introduced through the needle to administer the anesthetic and maintain the nerve block.

The above-described procedure is typically performed by an anesthesiologist in a prep room outside of the operating room (OR) because a period of time is necessary for the nerve block to become effective and because time in the OR is at a premium. This procedure is often very time consuming and inefficient due to the volume of medical supplies and items that must be obtained, opened and arranged in order to perform the nerve block.

First, the anesthesiologist must set up a sterile field around the desired pierce site. To do this, one or more packages containing the necessary supplies, such as a drape, iodine solution and prep sticks to apply the iodine solution, must be obtained and opened. Next, the epidural needle, infusion pump, infusion supplies (tubing, clamps, connectors, flow meter, filter, etc.), catheter and anesthetic, which are typically packaged separately, must be obtained and prepared. Additional medical supplies, such as a local anesthetic, needles and syringes are also necessary to numb the desired pierce site. These products are also likely to be packaged separately from each other, as well as from the supplies listed above.

The collection, opening and preparation of the above-listed medical supplies is time consuming and one or more items may be misplaced or forgotten. In addition, a large amount of waste is generated from the separately packaged items. Therefore, a need exists for an improved system of providing the primary medical supplies necessary to perform a continuous nerve block in a sterile and efficient manner.

SUMMARY OF THE INVENTION

One aspect of the present invention provides a pain management kit containing the primary supplies necessary to perform a continuous peripheral nerve block in a single, sterile container which may be easily stored and transported. Advantageously, the pain management kit is easy to open and its contents are arranged such that the items may be retrieved from the kit generally in the order of their subsequent use in the nerve block procedure.

Briefly stated, the pain management kit provides supplies necessary to create a sterile field, locally anesthetize the desired pierce site and perform the nerve block in a single, sterile container. Generally, the only additional supplies required are a nerve stimulator, an infusion pump, and the desired infusion drug. The nerve stimulator is an electronic device that is non-sterile and reusable, therefore it is not desirable to package it with the pain management kit. Likewise, the infusion pump may be an electronic device, but is preferably a mechanical pump. The infusion pump may also be reused, but, if of a typical mechanical variety, is inexpensive enough to be discharged with the patient. Because the infusion pump is reusable, and not required to be sterile, it is also desirably not included with the kit. Additionally, the choice of anesthetic drug may vary by doctor preference and/or patient need. Therefore, the drug is advantageously omitted from the pain management kit.

One embodiment provides a pain management kit with a plurality of medical items secured within a container configured such that the medical items remain sterile at least until the container is opened. The medical items include sterile field supplies, local anesthetic supplies and continuous nerve block supplies.

For purposes of summarizing the invention and the advantages achieved over the prior art, certain objects and advantages of the invention have been described hereinabove. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

Further aspects, features and advantages of the present invention will become apparent from the following drawings and detailed description intended to illustrate, but not to limit, the concepts of the invention.

DETAILED DESCRIPTION OF THE PREFERRED EMBODIMENT

The preferred embodiment of the pain management kit is illustrated in the context of a kit for use in performing a continuous nerve block such as, for example, but without limitation, an interscalene block, a lumbar plexus block or a femoral nerve block. However, as will be understood by those of skill in the art, the pain management kit can be used with other surgical procedures where it is desirable to provide sterile pain management medical supplies in a single package.

To assist in the description of the system and method of use disclosed herein, the following terms are used. The term "distal" refers to a site that is away from a specified site. The term "proximal" refers to a site that is close to a specified site. Expressed alternatively, a site termed "proximal" is measurably closer to a specified reference point than a site termed "distal." The term "downstream" refers to directional movement of the liquid drug from the infusion pump to the block site. An object or site referred to as "downstream" of another object or site means that the "downstream" object or site is proximal the block site relative to the other object or site. Similarly, an object or site referred to as "upstream" to another object or site means that the "upstream" object or site is proximal the infusion pump site relative to the other object or site. Expressed alternatively, the "downstream" object is proximal the block site and the "upstream" object is distal the block site.

The "block site" is the area within the body of the patient proximate the nerve bundle to be anesthetized. The "pierce site" is the site where the patient's skin is pierced to allow the epidural needle and, subsequently, the catheter to extend therethrough and arrive at the block site to administer the drug.

Description of the Pain Management Kit

Figure 1:
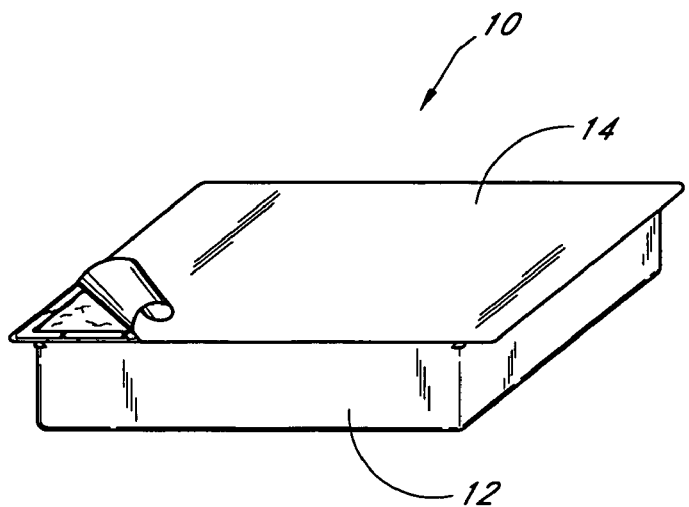
FIG. 1 illustrates a perspective view of a pain management kit generally containing the primary items necessary to perform a continuous nerve block.
Figure 2:
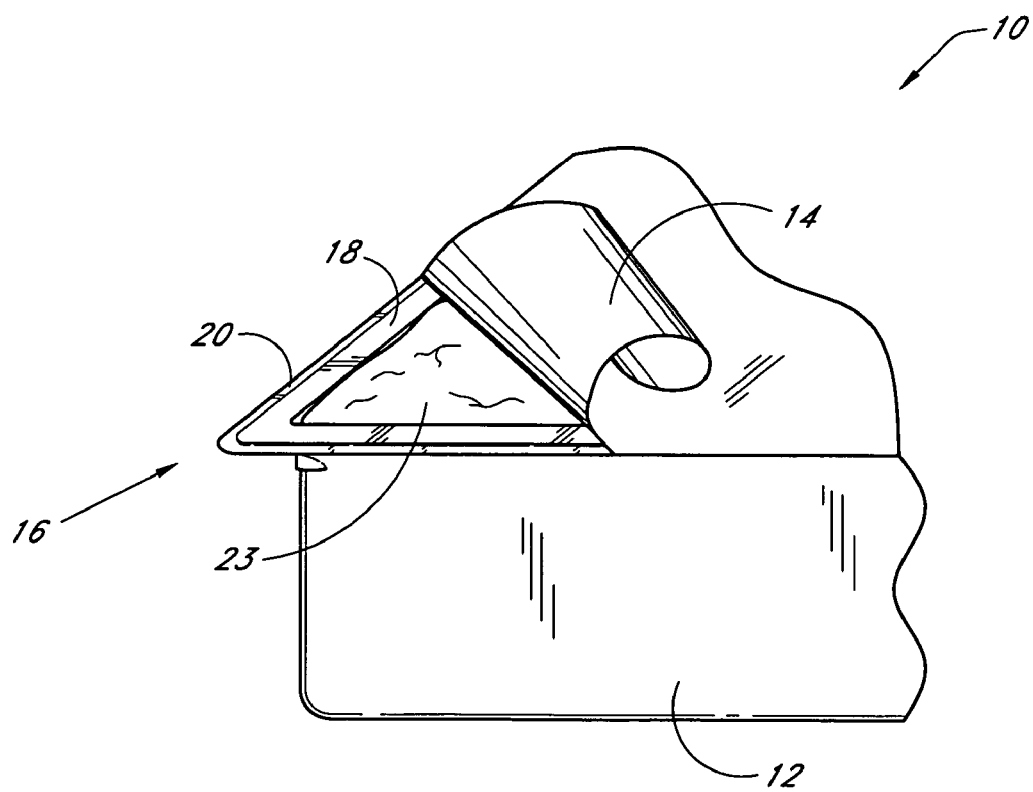
FIG. 2 is an enlarged view of the pain management kit of FIG. 1 illustrating the protective cover in a partially opened position and exposing a peripheral lip of the outer container.

With reference to FIGS. 1 and 2, a preferred pain management kit, generally indicated by the reference numeral 10, is illustrated. The contents of the kit 10 are contained within a relatively shallow, pan-shaped outer container 12. The outer container 12 is preferably a thermoplastic material suitable for use in a sterile medical environment and is preferably manufactured into a desired shape by thermoforming. However, other suitable materials and processes may be used to manufacture the outer container 12.

The outer container 12 includes a generally rectangular base and four side walls extending substantially normally upward therefrom. The side walls terminate in a peripheral lip 16 which defines a generally planar adhesive surface 18 and an integral, generally planar outer surface 20, which is preferably disposed at a height below the adhesive surface 18.

A protective cover 14, generally sized to be flush with the lip 16 of the outer container 12, is secured over the opening of the outer container 12. The protective cover 14 secures, and keeps sterile, the contents of the pain management kit 10 within the space between the outer container 12 and the protective cover 14. The protective cover 14 is preferably manufactured from a paper fiber material with a waterproof additive suitable for use in a sterile, medical environment. However, other suitable types of materials including, but not limited to, plastics or PVC may also be used in manufacturing the protective cover 14.

The protective cover 14 is secured to the adhesive surface 18 of the outer container 12, preferably with a non-toxic adhesive suitable for use in a sterile, medical environment. A desired adhesive would provide sufficient adhesive force to secure the protective cover 14 to the outer container 12 during storage and transport, while still allowing removal upon use without necessitating excessive removal force. Advantageously, a space is created between the outer surface 20 of the lip 16 and an edge portion 22 of the protective cover 14 to the outside of the adhesive surface 18. This arrangement allows the user of the kit 10 to grasp the edge portion 22 of the cover 14 to facilitate its removal from the outer container 12.

Figure 3:
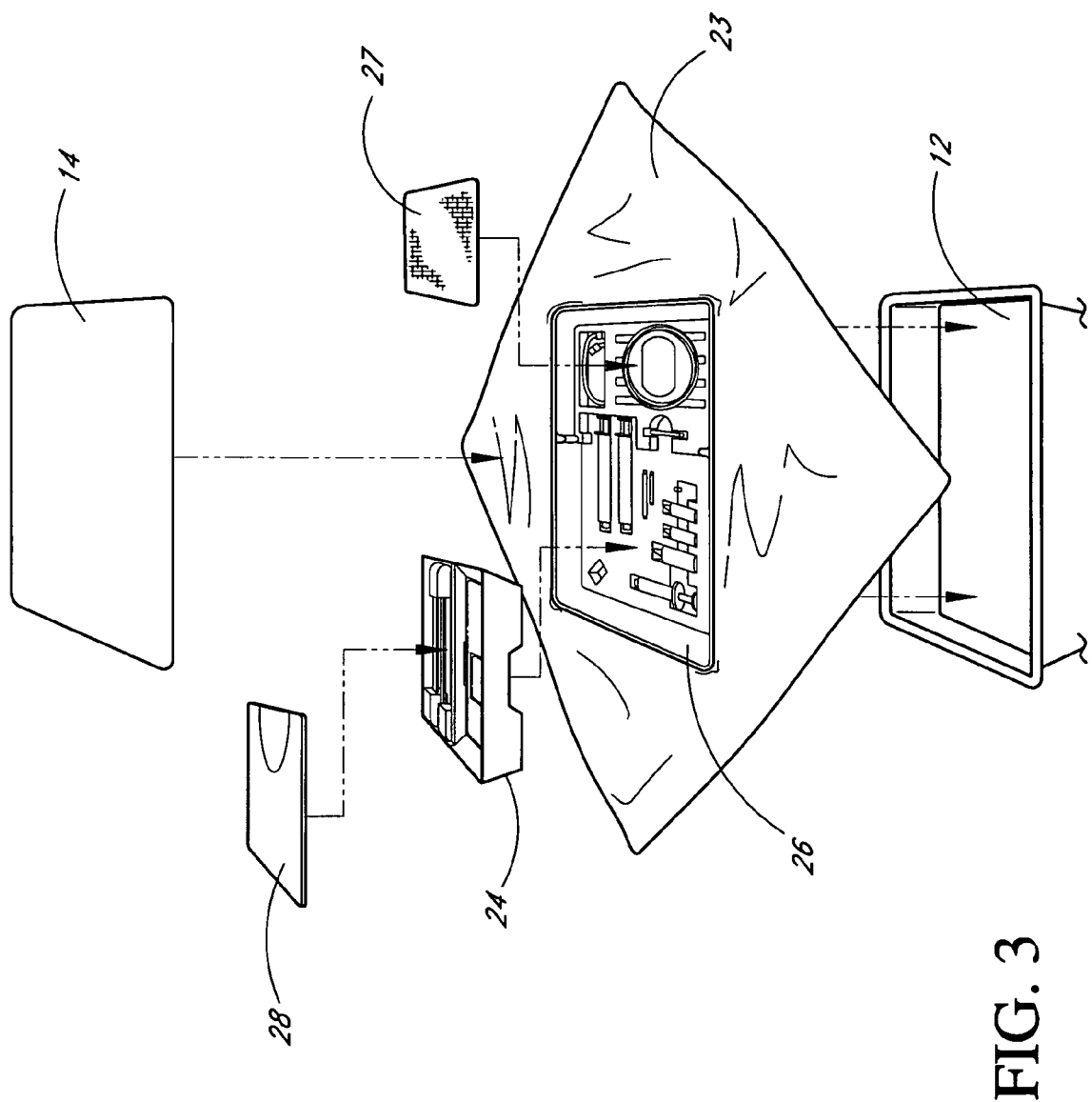
FIG. 3 is an exploded view of the pain management kit, including a sterile field tray and a main tray for holding certain items included in the kit.

With reference to FIG. 3, an exploded view of the pain management kit 10 is illustrated, with the protective cover 14 completely removed and the contents of the kit 10 removed therefrom.

Preferably, as packaged, a sterile wrap 23 is placed underneath the contents of the pain management kit 10, inside the outer container 12, and folded over to cover the contents of the kit 10 (FIG. 2). The sterile wrap 23 is preferably of a generally square shape and sized appropriately such that, when folded, the wrap 23 covers the entire contents of the pain management kit 10 and overlaps itself. Preferably, as illustrated, the corners of the sterile wrap 23 are aligned with the sides of the outer container 12. Each of the corners are folded over the contents of the kit 10 and toward the center of the outer container 12 to achieve the desired overlap of the sterile wrap 23 and substantially seal the contents of the pain management kit 10. The sterile wrap 23 may then be taped to itself in order to maintain the folded position.

In addition to the outer container 12, protective cover 14 and sterile wrap 23, the kit 10 also includes a sterile field tray 24 and a main tray 26. Similar to the outer container 12, the sterile field tray 24 and main tray 26 are preferably thermoformed from a thermoplastic material suitable for use in a sterile medical environment.

The contents of the kit, which are preferably the primary medical supplies for performing a continuous nerve block, and related preparatory procedures, are contained on or within the sterile field tray 24 and the main tray 26. The sterile field tray 24, advantageously, is held within a portion of the main tray 26 such that the top of the sterile field tray 24 is generally flush with the top of the main tray 26. In this manner, space within the outer container 12 of the pain management kit 10 is effectively utilized. However, the top of the sterile field tray 24 may also be located above or below the top of the main tray 26.

Figure 8:
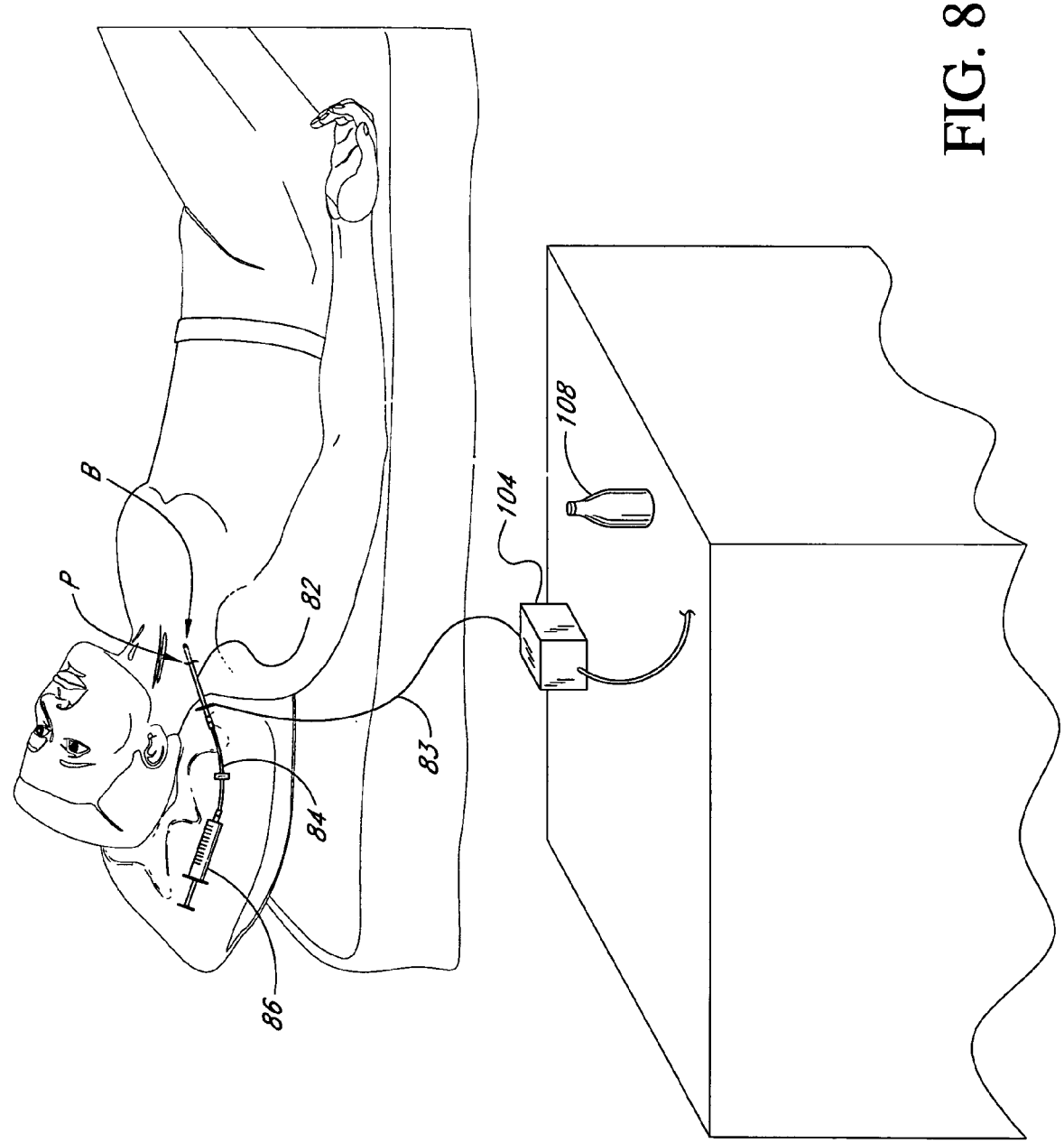
FIG. 8 is an illustration of a portion of the nerve block procedure using medical supplies contained in the kit of FIG. 1.

The sterile field tray 24 generally holds the medical supplies for creating a sterile field around the pierce site P (FIG. 8). The primary medical supplies for performing a local anesthetic procedure, as well as the nerve block procedure, and other general items are held within, or on, the main tray 26. Generally, the items in the kit 10 are disposed from top to bottom in the order in which they will be used in the normal course of the entire pre-operative nerve block procedure. Advantageously, this allows convenient access to the necessary medical supplies as they become needed, thus saving time and lending to an efficient, and uninterrupted, performance of the procedure.

With continued reference to FIG. 3, the illustrated sterile field tray 24 is nested to one side of the main tray 26 and disposed above additional medical supplies held within the main tray 26 such that the sterile field tray 24 is readily accessible without disturbing the other contents of the kit 10. This arrangement is advantageous because preparation of a sterile field around the desired pierce site P is typically the first step in a nerve block procedure and, as mentioned previously, the sterile field tray 24 preferably contains the necessary medical supplies to perform the entire sterile field preparation.

Preferably, an absorbent towel 27 is positioned on the side of the main tray 26 opposite the sterile field tray 24. The absorbent towel 27 is preferably constructed of a typical, disposable material suitable for use in a sterile, medical environment. Additionally, the towel 27 is a general use article and may be utilized throughout the nerve block procedure. Accordingly, the towel 27 is advantageously disposed at or near the top of the pain management kit 10.

A standard surgical drape 28 is provided, preferably, on top of the other contents of the sterile field tray 24. The drape may be a variety of shapes and sizes and preferably includes a cutout portion that may also vary in shape and size. As is conventional, the drape 28 is used to cover the area around where the nerve block is to be performed, while the cutout provides access to the desired pierce site P.

Figure 4:
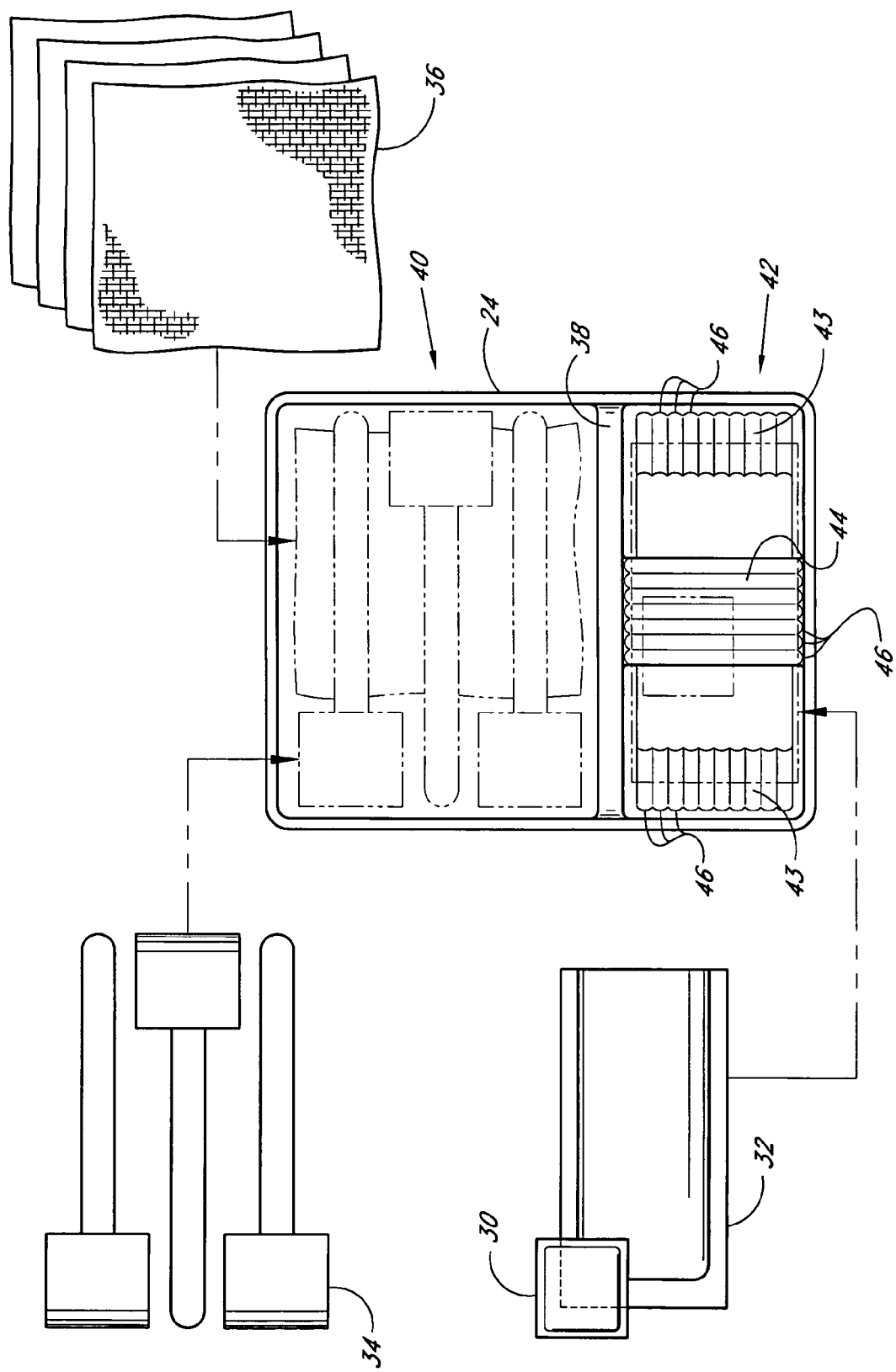
FIG. 4 is a top view of the sterile field tray of FIG. 3 with its preferred contents exploded therefrom. A preferred positioning of the contents within the sterile field tray is illustrated in phantom.

With reference to FIG. 4, the sterile field tray 24 and its remaining contents are illustrated in greater detail. The contents, in addition to the drape 28, preferably include a packaged skin prep pad 30, a package of iodine solution 32 and a plurality of prep sticks 34. The drape 28, along with the above-mentioned contents are sufficient to create a sterile field so that the remainder of the nerve block procedure may be performed. In the illustrated embodiment, three (3) prep sticks 34 are provided, however, this number may be adjusted in accordance with the requirements of the specific pain management procedure. In addition, one or more of the above-mentioned items may be omitted, or other desirable medical supplies may be provided in addition or in the alternative.

As illustrated in FIG. 4, a plurality of gauze pads 36 are also provided in the sterile field tray 24. Preferably, four (4)-8 ply, 4"×4" gauze pads 36 are provided in the sterile field tray 24 underneath the prep sticks 34. The gauze pads 36 are not necessarily utilized to establish the sterile field, but may be set aside, along with the tray 24, for later use.

The sterile field tray 24 preferably has a wall 38 that divides the tray 24 into two compartments 40, 42. The compartment 40 contains the prep sticks 34 and gauze pads 36, while the compartment 42 contains the skin prep pad 30 and iodine solution 32. The compartment 40 may additionally include a pair of angled side walls 43 and a central bridge 44, both of which desirably contain a plurality of strengthening ribs 46. The side walls 43, bridge 44 and ribs 46 all add structural integrity to the sterile field tray 24, allowing a minimum of material to be used in making the tray 24. Since the tray is disposable, this is advantageous in that less material is discarded and/or recycled.

The side walls 43 and bridge 44 also provide for ease of removal of the contents of the compartment 42, namely the skin prep pad 30 and iodine solution 32. The central bridge 44 supports the contents of the compartment 42 at a height above the base of the sterile field tray 24. Preferably, the skin prep pad 30 is on top of, and supported by, the package of iodine solution 32 such that it may easily be removed, leaving the iodine solution 32 supported by the bridge 44. One side of the iodine solution 32 may be pushed downward such that it pivots on the bridge 44, raising the opposite side of the package of iodine solution so that it can easily be withdrawn from the tray 24. The side walls 43 assist in this regard.

Figure 5:
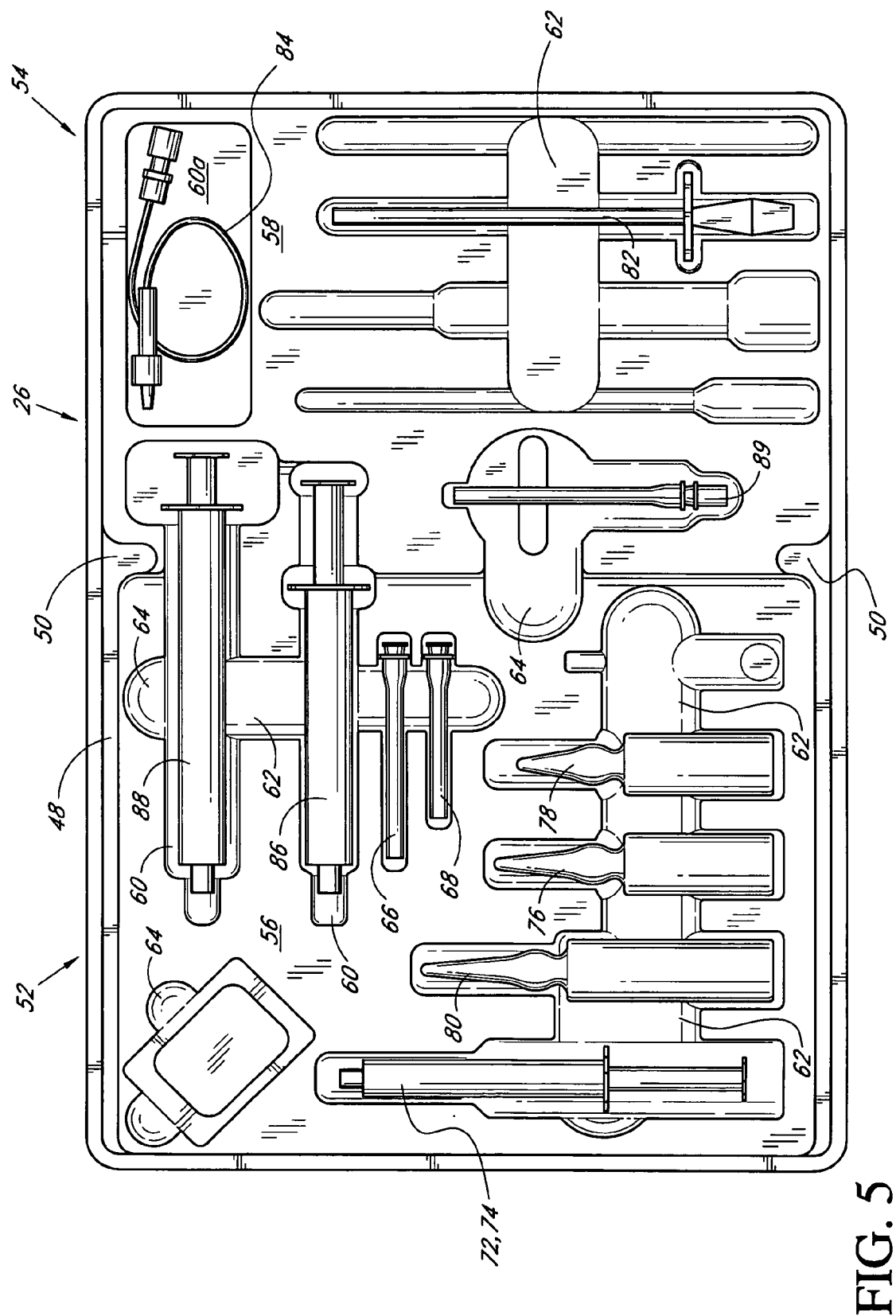
FIG. 5 is a top view of the main tray of FIG. 3 with its contents in a preferred arrangement.
Figure 6:
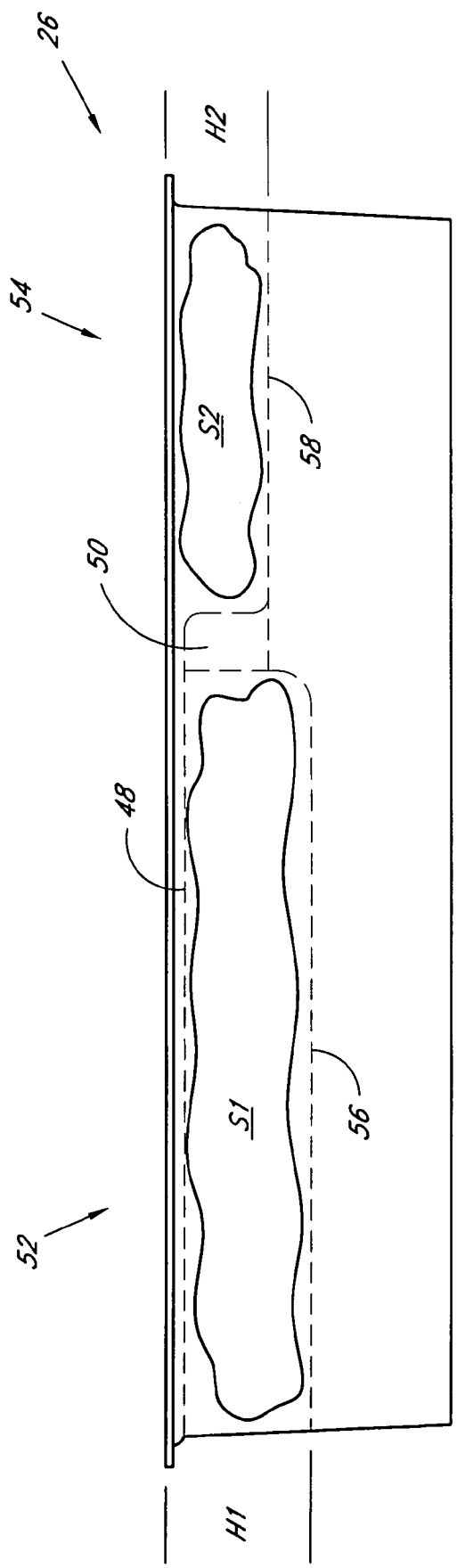
FIG. 6 is a side view of the main tray of FIG. 5, illustrating certain internal features in phantom.

FIGS. 5 and 6 present a more detailed illustration of the main tray 26. Preferably, the remaining contents of the kit 10 (i.e., the items for providing local anesthetic to the desired pierce site P and the primary nerve block items) are disposed within, or on, the main tray 26.

As mentioned previously, the sterile field tray 24 is desirably held within the main tray 26. Advantageously, the main tray 26 includes a support ledge 48 and a pair of stops 50 which are arranged to properly position the sterile field tray 24 and inhibit undesired movement. As illustrated in FIG. 6, the support ledge 48 is spaced below the top of the main tray 26 such that, when supporting a corresponding lip of the sterile field tray 24, the top of the sterile field tray 24 is generally flush with the top of the main tray 26.

Each of the pair of stops 50 protrudes from a wall of the main tray 26 and have a top surface which is generally planar with the support ledge 48. The stops 50 engage the sterile field tray 24 to hold it to one side of the main tray 26 and, in addition, generally define a pair of compartments 52, 54 within the main tray 26. The compartment 52 is generally located on the side of the stops 50 where the sterile field tray 24 is held while the compartment 54 occupies the adjacent side of the main tray 26.

As illustrated in FIG. 6, each compartment 52, 54 includes a generally planar floor 56, 58, respectively. The floor 56 of compartment 52 is at a lower height than the floor 58 of compartment 54. That is, there is a greater height difference between the top of the main tray 26 and the floor 56 than the height difference between the top of the main tray 26 and the floor 58. Accordingly, a height H1 of a space S1 between the floor 56 and the top of the main tray 26 is greater than the height H2 of a space S2 between the floor 58 and the top of the main tray 26. Advantageously, the height H1 is sized such that the floor 56 will not interfere with the bottom of the sterile field tray 24. Similarly, the height H2 is sized such that certain other supplies may be held within the space S2, as will be described below.

With reference to FIG. 5, a plurality of recesses 60 are formed into the main tray 26. The recesses 60 are shaped such that a corresponding item of the pain management kit 10 will fit within the recess 60 and, preferably, below the height of the floor 56, 58 that surrounds the recess 60. As illustrated, one or more of the recesses 60 may be disposed partially in each of the compartments 52, 54 of the main tray 26. Accordingly, such recesses 60 may be surrounded partially by each of the floors 56, 58, which are at different heights. In addition, a general recess 60a is provided which is generally rectangular in shape and may contain one or more items not necessarily of a corresponding shape.

Additionally, a plurality of access channels 62 and access depressions 64 are formed into the main tray 26 proximate to one or more recesses 60. Generally, the access channels 62 extend across, and connect, more than one recess 60, while the access depressions 64 communicate with a single recess 60. Both the access channels 62 and the access depressions 64 provide a space for fingers of a user of the pain management kit 10 when grasping a desired item and extract it from its recess 60.

Preferably, the items in the kit 10 that are relatively small and/or fragile (e.g., needles, syringes and vials) are held within a recess 60 of a generally corresponding size and shape. Other larger and/or less fragile items may be placed on top of the items contained in the recesses 60 in the spaces S1 or S2. As previously described, the sterile field tray 24 is preferably disposed within the space S1, while additional items may be disposed in the space S2, as is described below.

The remaining items in the illustrated pain management kit 10 fall into generally two categories: (1) medical supplies necessary or desired to perform a local anesthetic procedure and (2) medical supplies necessary or desired to perform the continuous nerve block procedure. These remaining items are generally contained in one of the recesses 60 or 60a and the space S2.

The local anesthetic supply contained in the kit 10 for performance of a local anesthetic procedure preferably includes a variety of needles, one or more vials of a local anesthetic, one or more vials of a sodium chloride solution and one or more syringes. In the presently illustrated embodiment, two needles 68, 70 are contained within the kit 10, including a 22 gage×1.5" needle 68 and a 25 gage×1.5" needle 70. Of course, needles of other sizes and diameters may be provided, as well as a greater or lesser quantity of needles, depending upon the desired application of the pain management kit 10.

The illustrated embodiment of the pain management kit 10 also contains a 3 cc plastic syringe 72 and a 5 cc plastic syringe 74. As will be appreciated by one of skill in the art, syringes of different sizes and material types may be substituted for the previously described syringes 72, 74, and a greater or lesser quantity of syringes may be included with the kit 10.

Additionally, the local anesthetic supply of the illustrated embodiment include a 5 ml vial of 1.0% Lidocaine solution 76 and a 5 ml vial of 1.5% Lidocaine solution 78 for use as a local anesthetic and a 10 ml vial of 0.9% Sodium Chloride solution 80. The Sodium Chloride solution 80 is useful to flush syringes and needles, as well as, a dilutant or solvent for other drugs, such as the Lidocaine solutions 76 or 78. Of course, other local anesthetic drugs and/or other dilutants or solvents may be used, in different strengths and quantities.

The nerve block supply contained within the pain management kit 10 preferably includes a Tuohy-type epidural needle 82, a needle extension assembly 84, a glass syringe 86, a plastic syringe 88, a filter needle 89, a catheter assembly 90 and an infusion system 92. Preferably, these supplies comprise the primary items necessary or desired to perform the continuous nerve block portion of the pain management procedure. A small number of additional, non-disposable supplies may also be necessary or desired, as will be described below.

The epidural needle 82 is preferably a 17 gage×3.5" Tuohy-type needle, as is known in the art. The epidural needle 82 preferably includes an integrated wire 83, or wires, constructed such that, when the wire 83 is connected to a power source, an electrical current may flow through the needle 82. Preferably, all but a distal tip portion of the needle 82 is insulated, such that substantially no current will pass from the needle to another conductive object, except through the uninsulated tip portion. Needles of the type described immediately above are commercially available.

The needle extension assembly 84 is a commercially available item primarily comprised of a tube with connectors at either end. A connector at one end of the needle extension 84 is preferably configured such that it will connect to the proximal end of the epidural needle 82. The other connector is preferably configured to connect to a variety of standard syringes. Thus, the needle extension assembly 84 is primarily useful for connecting a syringe to the epidural needle 82 and allowing fluid communication therebetween. In addition, a clamp may be provided on the needle extension assembly 84 which is operable to selectively compress the tube in order to occlude fluid flow.

The glass syringe 86 is preferably of a standard, 5 cc capacity variety. The glass syringe 86 is preferably capable of connection with the above-described needle extension assembly 84, thereby being useful to inject a liquid contained in the syringe 86, through the needle extension assembly 84 and epidural needle 82, to a desired nerve block site B (FIG. 8). In addition, the glass syringe 86, preferably, is also suitable for connection to one of needles 68, 70 for the purpose of loading the syringe 86 with a desired anesthetic from its vial.

The illustrated plastic syringe 88 is of a commercially available variety and preferably has a 10 cc capacity. The kit 10 additionally contains a filter needle 89, which is preferably a 19 gage×1.5" commercially available filter needle. In combination, the plastic syringe 88 and the filter needle 89 are useful to extract an anesthetic drug from a vial. The full syringe 88, with the needle 89 removed, may be directly connected to a suitable fill hub on the infusion system 92. In this manner, the syringe 88 may be used to fill a reservoir of the infusion system 92, as will be described in more detail below.

The illustrated catheter assembly 90 is a commercially available catheter suitable to transport a liquid drug from the infusion system 92 to the desired block site. The catheter 90 is also preferably suitable to be threaded through the epidural needle 82, in a known manner, to reach the desired block site. A proximal end of the catheter includes a removable connector 90a suitable to connect to a connector of the infusion system 92.

Figure 7:
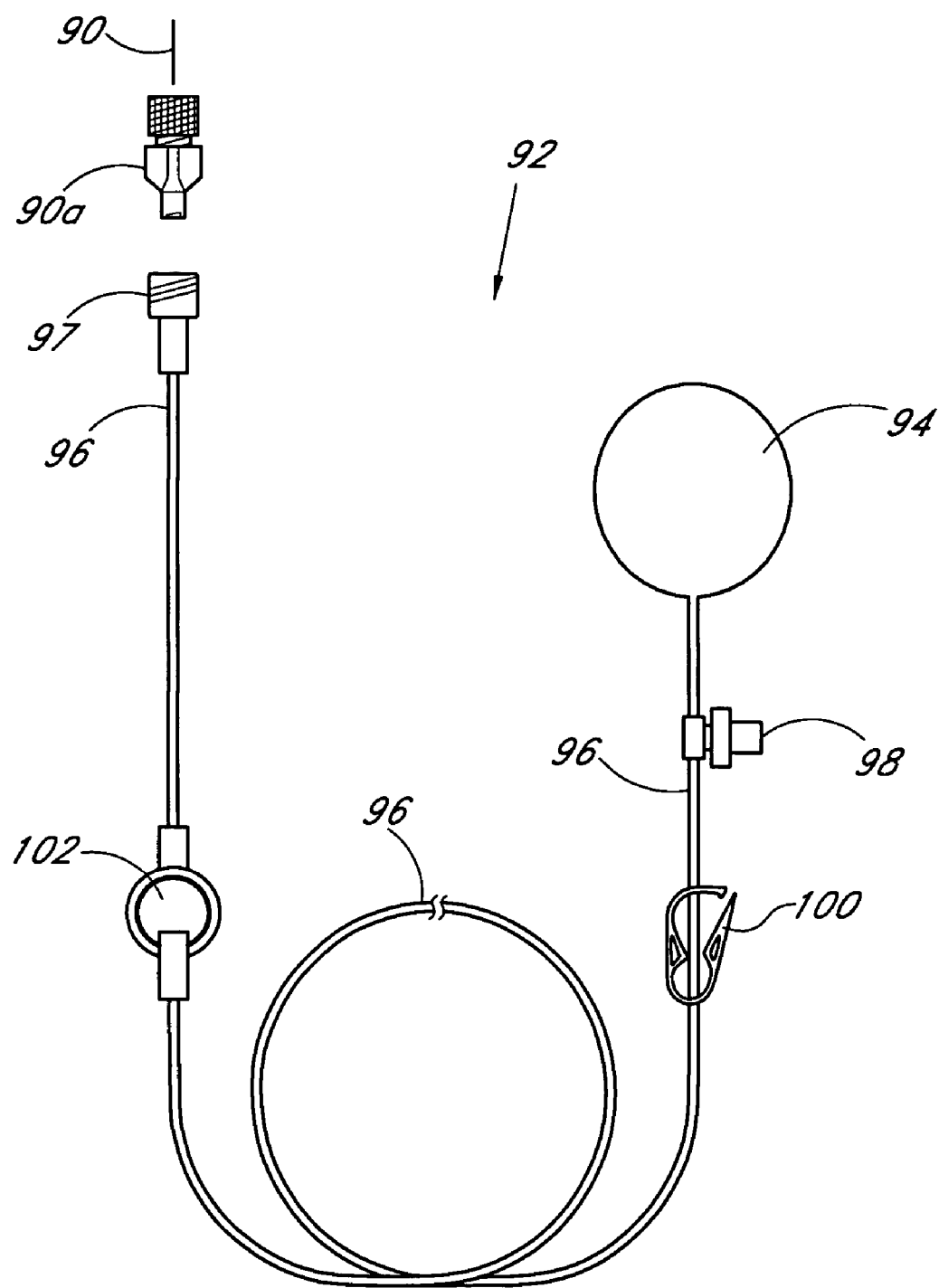
FIG. 7 is an illustration of an infusion system and catheter of the pain management kit of FIG. 1.

The infusion system 92 of the illustrated pain management kit 10 is also commercially available. With reference to FIG. 7, the infusion system 92 generally comprises a reservoir 94 in fluid communication with a length of medical tubing 96. The tubing 96 connects the reservoir 94 with a connector 97 suitable for connection to the connector 90a of the catheter 90, as described above. While stored within the kit 10, the infusion system 92 is preferably disposed generally in the space S2.

The infusion system 92 preferably also includes a catheter holder 95, which is capable of securing both the connector 97 of the infusion system 92 and the exposed portion of the catheter 90. Preferably, the catheter holder 95 has an adhesive backing suitable for use in a medical environment. Thus, the catheter holder 95 is useful to inhibit unintentional removal of the catheter 90. A preferred catheter holder 95 is commercially available under the brand name STATLOCK.

Preferably, a fill hub 98, a clamp 100 and a filter 102 are placed along the tubing 96, between the reservoir 94 and the connector 97. The fill hub 98 is capable of selectively permitting fluid communication between a syringe, such as the above-described syringe 88, and the lumen of the medical tubing 96. The clamp 100 is a conventional clamp which is suitable to selectively permit, or occlude, fluid flow within the tubing 96. The filter 102 is also commercially available and is suitable to separate the drug from any contaminates found in the drug. The filter is also suitable to eliminate air from the fluid path.

Figure 9:
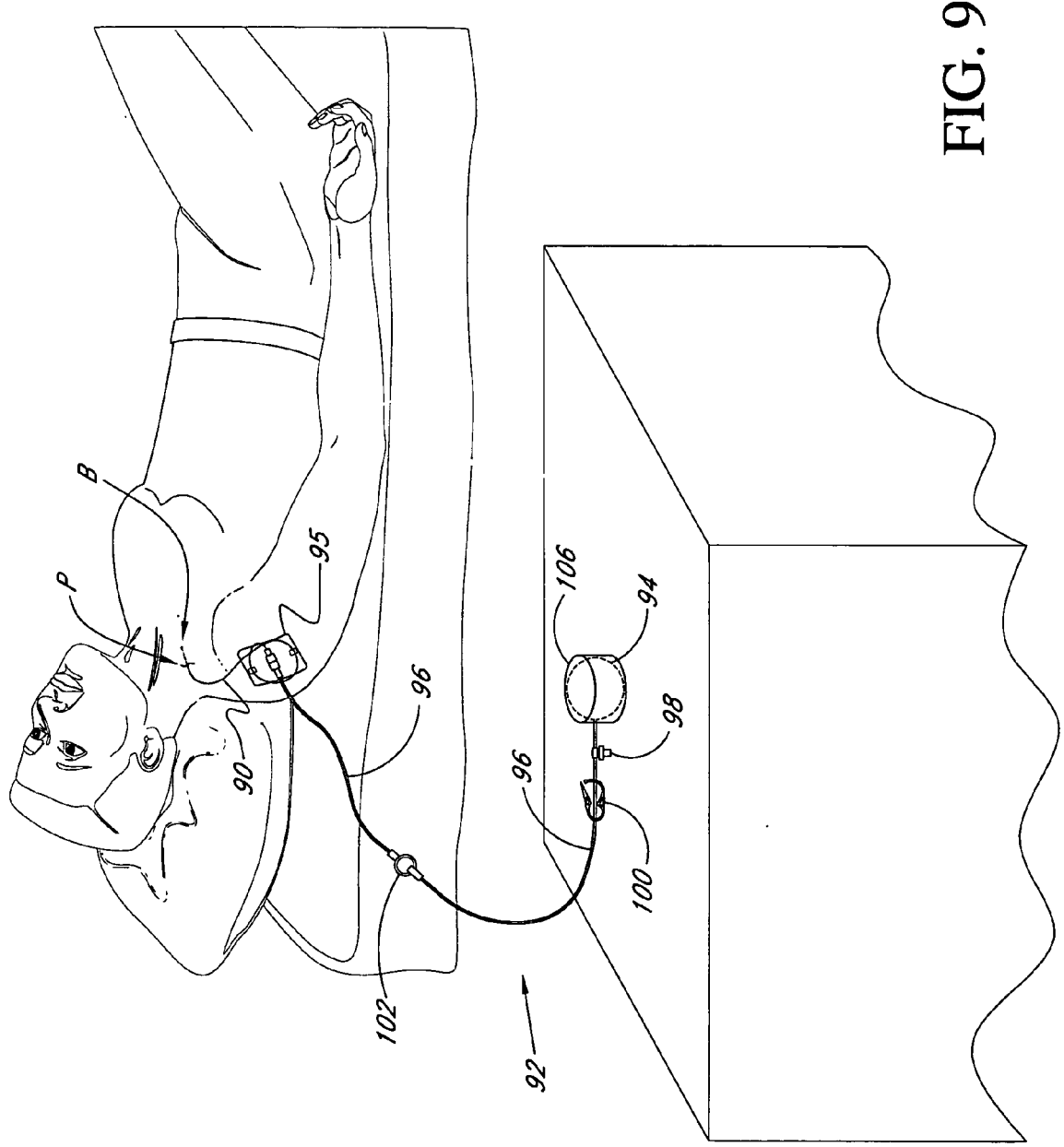
FIG. 9 is an illustration of a subsequent portion of the nerve block procedure using medical supplies contained in the kit of FIG. 1.

With reference to FIGS. 8 and 9, the items that are desirable for performing the pain management procedure and are not included in the pain management kit 10 generally comprise a nerve stimulator 104 (i.e., a current generating power source), an infusion pump 106, and the anesthetic 108. A desired nerve stimulator 104 is useful for generating a current to be applied to the epidural needle 82, as described above. A desired infusion pump 106 is useful for inducing a compressing force on the reservoir 94 of the infusion system 92 to expel a drug contained therein. The anesthetic drug 108 acts on the target nerve bundle to inhibit nerve signals from passing therethrough.

The nerve stimulator 104 is a non-sterile electronic device that is reusable. Therefore, it would be undesirable to include the nerve stimulator 104 in the otherwise disposable pain management kit 10. Similarly, the infusion pump 106 is reusable and, therefore, would also be undesirable to include in the kit 10. The anesthetic drug 108 is desirably not included with the pain management kit 10 because the choice of drug 108 may vary widely among practitioners using the kit 10.

Method of Using the Pain Management Kit

The contents of the pain management kit 10, individually, and their method of use, are generally known in the performance of continuous nerve blocks, and is understood by those of skill in the art. As such, the method of use of the kit 10 will be described only in general detail that is helpful to exemplify certain features and advantages of the pain management kit 10. Specifically, the method of use of the pain management kit 10 will be described in relation to an interscalene block procedure (i.e., a nerve block of the brachial plexus at the interscalene groove).

With primary reference to FIGS. 8 and 9, the continuous nerve block procedure is preferably performed in a prep room before the patient enters the OR. To begin the procedure, the protective cover 14 is removed from the outer container 12, exposing the sterile wrap 23 (FIG. 1). The tape is removed and the corners of the sterile wrap 23 are folded back to expose the sterile medical supplies contained within the pain management kit 10. The absorbent towel 27 may be removed for later use.

To create a sterile field, the drape 28 is removed from its place on the sterile field tray 24, and is unfolded and placed over the patient. The drape 28 is positioned such that the pierce site P is exposed within the cutout. For the purpose of clarity, the drape 28 has been omitted from FIGS. 8 and 9. The skin prep pad 30 is used to clean the patient's skin in the area surrounding the pierce site P. The iodine solution 32 is then applied to the skin surrounding the pierce site P with one or more of the prep sticks 34, in order to sterilize the pierce site P. Advantageously, the sterile field tray 24 may then be removed to expose the contents of the main tray 26.

To perform the local anesthetic procedure, one of the needles 68, 70 and one of the syringes 72, 74 are removed from their respective recesses 60 and assembled. One of the vials of Lidocaine 76, 78 are selected, removed from its recess 60 and opened. The syringe and needle assembly (not shown) is loaded with Lidocaine with the Sodium Chloride solution 80 being optionally used as a dilutant. An injection is then made proximate to the desired pierce site P to anesthetize the area for insertion of the epidural needle 82. The gauze pads 36 may be removed from the sterile field tray 24, which has been set aside, and used to control any bleeding that may occur due to the injection of local anesthetic.

To perform the actual nerve block portion of the procedure, first, the infusion system 92 is removed from the pain management kit 10, thereby exposing the other contents of the kit 10 disposed in the recesses 60, 60*a* disposed in compartment 54. The reservoir 94 of the infusion system 92 is filled with the anesthetic drug 108 by selecting the plastic syringe 88 and assembling the filter needle 89 thereto. The syringe/needle assembly 88/89 is then loaded with drug 108. The needle 88 is removed and the syringe 88 is connected to the fill hub 98 of the infusion system 92. The drug is then transferred from the syringe 88 to the reservoir 94. This procedure is repeated until the reservoir 94 is sufficiently full. Optionally, this step may be performed before the local anesthetic procedure, and the filled infusion system 92 may be set aside for later use.

With reference to FIG. 8, the epidural needle is removed from its recess 60 and the wire 83 of the epidural needle 82 is connected to the nerve stimulator 104. Next, the glass syringe 86 is removed from its corresponding recess 60 and is loaded with the anesthetic drug 108. The loaded glass syringe 86 is connected to the epidural needle 82 using the needle extension assembly 84 located in the pain management kit 10. The epidural needle 82 is inserted into the patient at the pierce site P and is advanced toward the block site B. The nerve stimulator 104 is activated such that current is pulsed through the epidural needle 82, preferably at about 0.2–0.5 milli-Amps (mA). The current through the needle 82 induces a motor response and when such a response is present at low current, proper placement of the epidural needle 82 is achieved. An injection of drug 108 from the glass syringe 86 is made and proper needle 82 placement is verified by a subsequent lack of motor response. Thereafter, the nerve stimulator 104 is shut down and the syringe 86 and needle extension assembly 84 are removed from the epidural needle 82.

The catheter 90 is inserted through the needle 82 until it reaches the desired block site B. The epidural needle 82 is withdrawn, leaving the catheter 90 in place. Next, the removable connector is assembled to the catheter 90. The filled infusion system 92 is connected to the catheter 90 and the reservoir 94 is placed in an infusion pump 106. The pump 106 is activated such that the drug 108 is expelled from the reservoir 94 and infusion system 92 through the catheter 90 and is delivered to the block site at a controlled rate. The drug 108 is administered in this manner over a period of time (e.g., 2–3 days). The portions of the pain management kit 10 remaining, including the outer container 12, protective cover 14, sterile field tray 24 and main tray 26, may then be disposed of in an appropriate manner, including recycling, if appropriate. Advantageously, the nerve stimulator 104 and the infusion pump 106 may be stored, or prepared, for use in a subsequent procedure.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the

What is claimed is:

1. A pain management kit for performing a nerve block procedure, comprising:
   a first tray having a bottom wall, a side wall extending from an entire periphery of said bottom wall, and an upper rim extending outwardly from an entire periphery of an upper end of said side wall, said first tray defining an interior space;
   a sterile wrap;
   a second tray positioned within said first trays;
   a third fray positioned within said second trays;
   a planar, protective cover releaseably attached to an entire periphery of said upper rim of said first tray to cover an open upper end of said first tray;
   wherein said sterile wrap includes a central portion positioned within said interior space of said first tray and a peripheral portion surrounding said central portion, said second tray positioned on top of said central portion of said sterile wrap, said second tray being sized and shaped to occupy a substantial entirety of said bottom wall of said first tray, a bottom wall of said second tray defining a plurality of recesses and being divided into a first portion and a second portion, wherein a first distance is defined between said upper rim and said first portion and a second distance is defined between said upper rim and said second portion, said first distance being greater than said second distance, said third tray positioned within said first portion of said second tray, a bottom wall of said third tray being sized and shaped to occupy a substantial entirety of said bottom wall of said first portion of said second tray and not extend into said second portion of said second tray;
   wherein said recesses of said second tray hold a collection of local anesthetic and continuous nerve block supplies and wherein said third tray holds a collection of sterile field supplies;
   wherein said peripheral portion of said sterile wrap is folded to cover said second tray and said third tray before said cover is attached to said first tray.

2. The kit of claim 1, wherein second tray includes a pair of stops between said first portion and said second portion, said stops configured to contact said third tray and prevent said third tray from moving into said second portion of said second tray.

3. The kit of claim 2, wherein said pair of stops are integrally formed with a side wall of said second tray.

4. The kit of claim 1, wherein said bottom wall of said third tray defines an area greater than one-half of an area defined by said bottom wall of said second tray.

5. The kit of claim 1, wherein said third tray includes an interior wall dividing an interior space of said third tray into a first section and a second section, wherein said first section is sized and shaped to accommodate a plurality of prep sticks.

6. The kit of claim 1, additionally comprising an adhesive-backed catheter holder, said catheter holder configured to secure an external section of said catheter to a patient.

7. The kit of claim 1, wherein both of said first tray and said second tray are rectangular in shape.

8. The kit of claim 7, wherein said third tray is rectangular in shape.

* * * * *